US009579415B2

(12) United States Patent
Brownlee et al.

(10) Patent No.: US 9,579,415 B2
(45) Date of Patent: Feb. 28, 2017

(54) JOINING AND/OR SEALING TISSUES THROUGH PHOTO-ACTIVATED CROSS-LINKING OF MATRIX PROTEINS

(75) Inventors: Alan George Brownlee, Salisbury (AU); Christopher Malcolm Elvin, Tennyson (AU)

(73) Assignee: Cook Incorporated, Bloomington, IN (US)

( * ) Notice: Subject to any disclaimer, the term of this patent is extended or adjusted under 35 U.S.C. 154(b) by 919 days.

(21) Appl. No.: 12/223,945

(22) PCT Filed: Feb. 14, 2007

(86) PCT No.: PCT/AU2007/000156
§ 371 (c)(1),
(2), (4) Date: Jan. 30, 2009

(87) PCT Pub. No.: WO2007/092998
PCT Pub. Date: Aug. 23, 2007

(65) Prior Publication Data
US 2009/0306707 A1    Dec. 10, 2009

(30) Foreign Application Priority Data

Feb. 14, 2006    (AU) ................................ 2006900770

(51) Int. Cl.
| | | |
|---|---|---|
| *A61K 31/74* | (2006.01) | |
| *A61K 9/00* | (2006.01) | |
| *A01N 25/34* | (2006.01) | |
| *A61B 17/08* | (2006.01) | |
| *A61F 13/00* | (2006.01) | |
| *A61L 24/10* | (2006.01) | |
| *C09J 189/00* | (2006.01) | |

(52) U.S. Cl.
CPC ............. *A61L 24/10* (2013.01); *A61L 24/106* (2013.01); *C09J 189/00* (2013.01)

(58) Field of Classification Search
None
See application file for complete search history.

(56) References Cited

U.S. PATENT DOCUMENTS

| | | | |
|---|---|---|---|
| 4,474,851 A | 10/1984 | Urry | |
| 4,600,574 A | 7/1986 | Lindner et al. | |
| 5,713,891 A | 2/1998 | Poppas | |
| 6,495,127 B1 * | 12/2002 | Wallace et al. | 424/78.03 |
| 6,607,522 B1 * | 8/2003 | Hamblin et al. | 606/8 |
| 6,613,582 B1 | 9/2003 | Kodadek et al. | |
| 2002/0192636 A1 * | 12/2002 | Guarino et al. | 435/4 |
| 2003/0013080 A1 * | 1/2003 | Luebke et al. | 435/5 |
| 2003/0032143 A1 | 2/2003 | Neff et al. | |
| 2004/0101548 A1 * | 5/2004 | Pendharkar | 424/445 |

FOREIGN PATENT DOCUMENTS

| | | |
|---|---|---|
| WO | WO 92/13025 | 8/1992 |
| WO | WO 94/21306 | 9/1994 |
| WO | WO 97/42986 | 11/1997 |
| WO | WO 02/058750 A2 | 8/2002 |
| WO | WO03/037248 | 5/2003 |
| WO | WO2004/104042 | 12/2004 |
| WO | WO2007/092998 | 8/2007 |

OTHER PUBLICATIONS

Luebke et al.; J Biomed Mater Res 68A: 696-703, 2004.*
US Patent Documents—None.*
Non-Patent Documents—None.*
Search Report and Written Opinion for PCT Application No. PCT/AU2007/000156, 8 pages, Mar. 16, 2007.
Brown, K.C. and Kodadek, T., "Protein Cross-Linking Mediated by Metal Ion Complexes", T Met Ions Biol Syst. 2001; 38:351-84.
Dickneite, G., H. J. Metzner, M. Kroez, et al. "The Importance of Factor XIII as a Component of Fibrin Sealants." Journal of Surgical Research 107 (Oct. 2002): 186-195.
Dodd, R. A., R. Cornwell, N. E. Holm, et al. "The Vivostat Application System: A Comparison with Conventional Fibrin Sealant Application Systems." Technology and Health Care 10 (2002): 401-411.
D A. Fancy and T. Kodadek "Chemistry for the Analysis of Protein-Protein Interactions: Rapid and Efficient Cross-Linking Triggered by Long Wavelength Light." Proc. Natl. Acad. Sci. vol. 96, pp. 6020-6024, May 1999.
Jackson, M. R. "Fibrin Sealants in Surgical Practice: An Overview." American Journal of Surgery 182 (Aug. 2001) (2 Suppl) : 1S-7S.
Khadem. J., Veloso, A.A., Tolentino, F.T., Hasan, T. and Hamblin, M.R., "Photodynamic Tissue Adhesion with Chlorine$_{e6}$ Protein Conjugates." IOVS, Dec. 1999, vol. 40, No. 13.
Lee, K-C, Park, S-K and Lee, K-S (1991) "Neurosurgical Applications of Fibrin Sealants", Yonsei Medical Journal vol. 32, No. 1, 1991, pp. 53-57, 9th Annual Congress of the World Society of Cardio-Thoracic Surgeons; Nov. 1999, Lisbon, Spain.
Mankad, P. S., and M. Codispoti. "The Role of Fibrin Sealants in Hemostasis." American Journal of Surgery 182 (Aug. 2001) (2 Suppl): 21S-28S.
Marone, P., Monzillo V., Segu C., and Antoniazzic E., "Antibiotic-Impregnated Fibrin Glue in Ocular Surgery:In vitro Antibacterial Activity", Ophthalmologica 1999; 213:12-15.
Matras, H., "Fibrin Seal: The State of the Art", J. Oral Maxillofac. Surg. 43: 605-611 (1985).
Milne, A. A., Murphy, W. G., Reading, S. J., and Ruckley, C. V., "Fibrin Sealant Reduces Suture Line Bleeding During Carotid Endarterectomy: A Randomised Trial", Eur. J. Endovasc. Surg. 10: 91-94 (1995).

(Continued)

*Primary Examiner* — Jeffrey T Palenik
(74) *Attorney, Agent, or Firm* — Woodward, Emhardt, Moriarty, McNett & Henry LLP; Joshua Astin

(57) ABSTRACT

A method of joining and/or sealing tissues in a surgical procedure or medical treatment, comprising the steps of: (1) applying a matrix protein, a photoactivatable metal-ligand complex and an electron acceptor to a tissue portion; (2) irradiating said tissue portion to photactivate the photoactivatable metal-ligand complex: thereby initiating a cross-linking reaction of the matrix protein to seal said tissue portion or join said tissue portion to an adjacent tissue portion.

7 Claims, 14 Drawing Sheets

(56) References Cited

OTHER PUBLICATIONS

Morikawa, T. "Tissue Sealing", American Journal of Surgery 182 (Aug. 2001) (2 Suppl): 29S-35S.
Nishimotol Kazuo, Yamamura Keiko, Fukase Fumiaki, Kobayashil Masayoshi, Nishikimil Naomichi and Komoril Kimihiro, "Subcutaneous Tissue Release of Amikacin from a 15 Fibrin Glue/Polyurethane Graft", Journal of Infection and Chemotherapy; vol. 10, No. 2 (2004) pp. 101-104.
Spotnitz, W.D., "Fibrin Sealant in the United States: clinical use at the University of Virginia", Thrombosis Haemostasis 74(1) 482-485 (1995).
Yoshida H., Yamaoka Y., Shinoyama M., "Novel Drug Delivery System Using Autologous Fibrin Glue-Release Properties of Anti-cancer Drugs", Biol. Pharm. Bull. 23(3) 371-374 (2000); Department of Pharmacy, Yamaguchi University Hospital, Ube, Japan.
Communication from European Patent Office issued in application PCT/AU2008/001178 dated Nov. 15, 2012.
International Search Report and Written Opinion for PCT Application No. PCT/AU2008/001178, 11 pages, Sep. 5, 2009.
International Preliminary Report on Patentability for PCT Application No. PCT/AU2008/001178, 9 pages, Feb. 25, 2010.
Barnes C P, Smith M J, Bowlin G L, Sell S A, Tang T, Matthews J A, Simpson D G, Nimtz J C "Feasibility of Electrospinning the Globular Proteins Hemoglobin and Myoglobin" Journal of Engineered Fibers and Fabrics vol. 1 No. 2, 16-29 (2006).
David A Fancy, Carilee Denison, Kyonghee Kim, Yueqing Xie, Terra Holdeman, Frank Amini and Thomas Kodadek "Scope, limitations and mechanistic aspects of the photo-induced cross-linking of proteins by water-soluble metal complexes" Chemistry & Biology (2000) 7:697-708.
Furst W, Banerjee A, Redl H. Comparison of structure, strength and cytocompatibility of a fibrin matrix supplemented either with tranexamic acid or aprotinin. J Biomed Mater Res B Appl Biomater. (2007) 82:109-14.
Kodadek T, Isabelle Duroux-Richard and Jean-Claude Bonnafous, "Techniques: Oxidative cross-linking as an emergent tool for the analysis of receptor-mediated signalling events" TRENDS in Pharmacological Sciences vol. 26 No. 4 Apr. 2005.
Lee MG, Jones D. "Applications of fibrin sealant in surgery." Surg Innov. 2005; 12:203-213.
Makogonenko E, Ingham K C, Medved L. Interaction of the fibronectin COOH-terminal Fib-2 regions with fibrin: further characterization and localization of the Fib-2-binding sites. Biochemistry. May 8, 2007; 46(18):5418-26. Epub Apr. 11, 2007.
McManus, M, Sell S A, Espy P G, Koo, H P and Bowlin G L (2006) "On the Road to in situ Tissue Regeneration: A Tissue Engineered Nanofiber Fibrinogen-Polydioxanone Composite Matrix" Proceedings of Mid-Atlantic section of the American Urological Association Annual Meeting, 2006 www.maaua.org/abstracts/2006/07.cgi.
Mosesson M W, Fibrinogen and fibrin structure and functions. J Thromb Haemost. (2005) 3:1894-904;
Mosesson M W, Siebenlist K R, Meh D A. The structure and biological features of fibrinogen and fibrin. Ann N Y Acad. Sci. 2001; 936:11-30).
Velada J L, Hollingsbee D A, Menzies A R, Cornwell R, Dodd R A. Reproducibility of the mechanical properties of Vivostat system patient-derived fibrin sealant. Biomaterials. May 2002; 23(10):2249-54.
Weisel JW, "Fibrinogen and fibrin", Adv Protein Chem. 2005;70:247-299.
U.S. Appl. No. 12/673,400, filed Feb. 12, 2010.
Office Action issued for U.S. Appl. No. 12/673,400 on Jul. 17, 2012.
Australian Examination Report dated Apr. 17, 2012 for corresponding Australian Patent Application No. 2007215382, 2 pages.
Australian Examination Report dated Dec. 1, 2012 for corresponding Australian Patent Application No. 2008286700, 3 pages.
Canadian Office Action dated Mar. 6, 2013 for corresponding Canadian Application No. 2,640,560, 2 pages.
Canadian Office Action dated Jul. 4, 2013 for corresponding Canadian Application No. 2,696,255, 4 pages.
European Search Report and Written Opinion dated Nov. 8, 2012 for corresponding European Application No. 08 782 926.3, 7 pages.
Indian Examination Report dated Aug. 16, 2013 for corresponding Indian Application No. 7056/DELNP/2008, 2 pages.
Office Action issued for Japanese Application No. 2008-554565 dated Jun. 5, 2012.

* cited by examiner

JOINING AND/OR SEALING TISSUES THROUGH PHOTO-ACTIVATED CROSS-LINKING OF MATRIX PROTEINS

This application is a filing under 35 U.S.C. §371 of International Patent Application PCT/AU2007/000156, filed Feb. 14, 2007, which claims priority to Australian application no. AU 2006900770, filed Feb. 14, 2006.

TECHNICAL FIELD

The present invention relates to a method of joining and/or sealing tissues in surgical procedures and medical methods, and compositions for use in said methods.

BACKGROUND ART

Tissue adhesives have been suggested as alternatives in surgical procedures to physical means of connecting tissues such as sutures and staples. Tissue adhesives will hold cut or separated areas of tissue together to allow healing and/or serve as a barrier to leakage, depending on the application. The adhesive should break down or be resorbed and it should not hinder the progress of the natural healing process. Ideally, the agent should promote the natural mechanism of wound healing and then degrade.

Tissue adhesives are generally utilized in three categories:
i) Hemostasis (for example, by improving in vivo coagulation systems, tissue adhesion itself has a hemostatic aim and it is related to patient clotting mechanisms)
ii) Tissue sealing: primary aim is to prevent leaks of various substances, such as air or lymphatic fluids.
iii) Local delivery of exogenous substances such as medications, growth factors, and cell lines.

A number of classes of tissue adhesives have been investigated and used:
Fibrin sealants (otherwise referred to as fibrin glues)
Albumin-based compounds (glutaraldehyde glues)
Cyanoacrylates
Hydrogels (polyethylene glycol polymers)
Collagen-based adhesives Fibrin glue was first used for hemostasis in 1909. Fibrin glues were initially homemade in the operating room by surgeons, but became commercially available in Europe in the early 1980s and are now in widespread use. Overall, fibrin sealants are very well tolerated by patients (Spotnitz, 1995; Lee et al, 1991; Milne et al, 1995)

One accepted value of fibrin glues lies in their unique physiologic action, which mimics the early stages of the blood coagulation process and wound healing; the part of the normal coagulation cascade to produce an insoluble fibrin matrix. Fibrinogen is a plasma protein with a molecular weight of 340,000. The fibrinogen molecule consists of two identical subunits that each contains one alpha, beta, and gamma polypeptide chain linked by disulfide bonds. In the natural mechanism, fibrinogen polypeptides are cleaved to soluble fibrin monomers by the action of activated thrombin. These monomers are cross-linked into an insoluble fibrin matrix with the aid of activated factor XIII (FIG. 1). The adhesive qualities of consolidated fibrin sealant to the tissue may be explained in terms of covalent bonds between fibrin and collagen, or fibrin, fibronectin and collagen. Fibrin glues act as both a hemostatic agent and as a sealant. They are bioabsorbable (due to in vivo thrombolysis). Degeneration and reabsorption of the resulting fibrin clot is achieved during normal wound healing.

All fibrin sealants in use as of 2003 have two major ingredients, purified fibrinogen (a protein) and purified thrombin derived from human or bovine blood. Many sealants have two additional ingredients, human blood factor XIII and a substance called aprotinin, which is derived from cows' lungs. Factor XIII is a compound that strengthens blood clots by forming covalent cross-links between strands of fibrin. Aprotinin is a protein that inhibits the enzymes that break down blood clots.

The preparation and application of fibrin sealants are somewhat complicated. The thrombin and fibrinogen are freeze-dried and packaged in vials that must be warmed before use. The two ingredients are then dissolved in separate amounts of water. Next, the thrombin and fibrinogen solutions are loaded into a double-barreled syringe that allows them to mix and combine as they are deposited on the incision. Pieces of surgical gauze or fleece may be moistened with the sealant solutions to cover large incisions or stop heavy bleeding. Recent developments include a delivery system that forms a fibrin sealant from the patient's own blood within a 30-minute cycle, and uses a spraypen rather than a double-barreled syringe for applying the sealant. Nevertheless there remains the difficulty that the seal takes a significant period of time to form and reach strength sufficient to hold when under pressure. Typically 70% of its ultimate strength is reached in 10 minutes, and full strength in approximately 2 hours, which means that fibrin sealants are unsuitable for many applications (for example, sealing an incision in a blood vessel, since prolonged clamping would be required) and inconvenient in many other applications compared to traditional methods.

The use of tissue adhesives is one alternative method to traditional mechanical means for closing incisions. A second technique known as laser tissue welding relies on carbon dioxide or Nd: YAG lasers to produce thermal effects to "weld" tissue surfaces together. A variant of this technique is referred to as chromophore-assisted laser welding and uses a protein solder that contains a light-absorbent dye together with a laser that emits the appropriate wavelength light. Thus for example the dye fluorescein is used in combination with a 532 nm frequency-double Nd: YAG laser or indocyanine green is used with an 805 nm diode laser. In this technique the energy absorbed by the dye was generally thought to be released as heat so as to denature proteins and produce non-covalent bonds between the added protein solder and collagen in the surrounding tissue. However, Khadem et al. (1999) suggested that, depending on the dye used, there may be contributions from photochemical reactions that produce covalent cross-links between protein molecules. To test this hypothesis Khadem et al. prepared covalent conjugates between the dye chlorin$_{e6}$ and a globular, non-structural protein, bovine serum albumin (BSA). They found that a fibrinogen conjugate with chlorin$_{e6}$ was substantially aggregated and unsuitable for use as a solder. Therefore, to explore the effect of fibrinogen on weld strength, they mixed fibrinogen with bovine serum albumin-chlorin$_{e6}$ conjugate in one experiment and with free chlorin$_{e6}$ in another. Khadem et al. concluded that these solders performed particularly poorly compared to a BSA-chlorin$_{e6}$ conjugate. Thus the inclusion of the matrix protein fibrinogen in the mixture adversely affected the results achieved with a BSA-chlorin$_{e6}$ conjugate.

In U.S. Pat. No. 6,607,522 (Hamblin & Khadem) there is disclosed a method of welding tissue together comprising applying to at least one tissue a composition including a photosensitizer and a proteinaceous compound or lipid and irradiating the composition to promote adhesion of the tissue to a second tissue. Note the term "photosensitizer" as used therein refers to a compound capable of undergoing photo-activation by converting electromagnetic radiation into chemical energy in the form of reactive oxygen species like singlet oxygen, superoxide anion, hydroxyl radicals and the like. As in the Khadem paper, a fibrinogen conjugate with chlorin$_{e6}$ was prepared but was found to be substantially aggregated and unsuitable for use as a solder. Therefore, fibrinogen was mixed with a BSA-chlorin$_{e6}$ conjugate and with free chlorin$_{e6}$ to produce similarly poor results to those reported in the Khadem paper.

A photoactivable tissue sealant known as FOCALSEAL has been developed and is FDA approved. FOCALSEAL is a polyethylene glycol based synthetic hydrogel which has two components, a primer and a sealant, and is applied in two steps and then polymerised by the application of a blue-green light. The sealant does not bond covalently to tissue but rather creates a mechanical bond that requires interpolation of sealant into an irregular tissue surface. The sealant is a macromer consisting of a water-soluble polyethylene glycol molecule, a biodegradable polylactic acid, trimethylene carbonate, and a polymerizible acrylic ester. An eosin-based primer penetrates the tissue, cross-links with itself, and provides a mechanical interlink to the sealant compound. The primer and sealant work in unison; the primer provides tissue penetration and tissue clearance and the sealant contributes desirable elastic properties. The primer also helps initiates the photo-polymerization of the sealant's acrylic ester group upon exposure to the light source.

SUMMARY OF THE INVENTION

The present inventors have recognised that the natural strong self-association of matrix proteins would likely result in the inter- and intra-molecular conjunction of a number of individual aromatic amino acid residues such as tyrosine and histidine, most particularly, tyrosine residues. They have inferred that this would render self-associated matrix proteins susceptible to covalent bonding and polymerisation using a photoactivatable catalyst capable of inducing formation of a stablilised free radical on adjacent aromatic side chains so as to initiate formation of a carbon-bond between the two. Consequently they have successfully cross-linked matrix proteins in a photo-initiated chemical process in which a metal-ligand complex in conjunction with an electron acceptor directly mediates cross-linking between adjacent proteins through a mechanism which does not involve formation of potentially detrimental species such as singlet oxygen, superoxide or hydroxyl radicals. While not wishing to be bound by theory, it is believed that the mechanism involves irradiation of the metal-ligand complex to induce an excited state, followed by transfer of an electron from the metal to an electron acceptor. The oxidised metal then extracts an electron from a side chain such as tyrosine side chain in the matrix protein to produce, a tyrosyl radical which reacts immediately with a nearby tyrosine to form a dityrosine bond. A direct cross-link (without any bridging moiety) is created quickly in this photo-initiated chemical reaction, without the need for introduction of a primer layer and without the generation of potentially detrimental species such as singlet oxygen, superoxide and hydroxyl radicals.

Accordingly, a first aspect of the present invention provides a method of joining and/or sealing tissues in a surgical procedure or medical treatment, comprising the steps of:

(1) applying a matrix protein, a photoactivatable metal-ligand complex and an electron acceptor to a tissue portion;

(2) irradiating said tissue portion to photoactivate the photoactivatable metal-ligand complex;

thereby initiating a cross-linking reaction of the matrix protein to seal said tissue portion or join said tissue portion to an adjacent tissue portion.

The method may involve moving the said tissue portion to a position adjacent, inclusive of touching, the adjacent tissue portion, where necessary, such as when a relatively large gap exists between them. Alternatively, the matrix resulting from the cross-linking reaction may form a plug which nevertheless binds the tissues to either side of an incision or opening. Furthermore, the cross-linked matrix may form a coating over a region of tissue, and may be shaped or supported as appropriate, for example, the matrix protein, photoactivatable metal-ligand complex and electron acceptor may be carried by a collagen sheet or impregnated in a surgical gauze or fleece. Accordingly, it will be appreciated that the cross-linked matrix can adopt a physical form to suit the application in which it is used, and it will be applied in the appropriate manner to suit that purpose.

In an embodiment the method is used to seal a vessel. This may be to seal blood vessels to prevent blood loss, to treat lung tissue for sealing air leaks, to prevent cerebrospinal fluid leakages or to seal a vessel to prevent leakage of any other biological fluid.

In an embodiment the method is used to join a first tissue portion and a second tissue portion to seal a wound such as an incision, for example, in aesthetic surgery.

In an embodiment the method is used to treat a soft tissue such as liver or lung tissue which has suffered injury, for example, by coating the tissues.

Tissue adhesives of the present invention may also be used as wound dressings, for example, if applied alone or in combination with adhesive bandages, or as a haemostatic dressing in the operating room.

Accordingly, in a second aspect of the invention there is provided a closure for a bleeding wound comprising a substrate suitable for application to a wound to stem bleeding, wherein said substrate is impregnated or coated with one or more of a maxtrix protein, a photoactivatable metal-ligand complex and an electron acceptor.

In an embodiment the substrate is a bandage, gauze, cloth, tampon, membrane or sponge.

According to a third aspect of the present invention there is provided a method of stemming bleeding from a wound comprising applying a closure as described above to a bleeding wound, and irradiating the closure and surrounding tissue, thereby causing a cross-linking reaction between one or more matrix proteins within or coating the closure and the surrounding tissue to join the closure to the surrounding tissue.

According to a fourth aspect of the present invention there is provided a composition comprising a matrix protein, or administration thereof, a photoactivatable metal-ligand complex and an electron acceptor.

According to a fifth aspect of the present invention there is provided a kit comprising a matrix protein, or administration thereof, a photoactivatable metal-ligand complex and an electron acceptor.

In an embodiment the matrix protein, metal-ligand complex and an electron acceptor is separately contained within the kit.

The kit optionally contains buffer, such as phosphate buffered saline, for preparation of solutions of one or more matrix proteins, photoactivable metal-ligand complex and electron acceptor. The kit may include a weak acid such as acetic acid to render an otherwise insoluble matrix protein such as fibrin soluble.

A light source may also be provided in the kit, particularly where the kit is for use in the field.

In an embodiment a wound closure such as a bandage, gauze, cloth, tampon, membrane or sponge may be provided in the kit and, optionally, maybe pre-impregnated or pre-coated with one or more of a matrix protein, a photoactivable metal-ligand complex and an electron acceptor.

In an embodiment, a composition comprises one or more matrix proteins, a photoactivable metal-ligand complex and an electron acceptor and inert carrier. In particular, these compounds are dissolved in an inert carrier, and a solution comprising all three components is applied to the tissue portion. In particular, the solution is an aqueous solution, and generally a solution in a buffer such as phosphate buffered saline. Alternatively, each of the three components could be applied separately, or as separate solutions, prior to irradiation.

The method of application is not critical and may involve spreading of a solution over the appropriate tissues or over a region to be sealed or rubbing of one tissue portion on another to spread the solution.

In an embodiment a drug (particularly a chemotactic, growth promoting or differentiation factor but also a conventional drug such as an antibiotic or chemotherapeutic drug) or other therapeutic agent is applied to said first tissue portion and/or said second tissue portion, in particular, as a component of the composition described above. While not wishing to be bound by theory it is believed that the therapeutic agent is captured in the matrix formed by the cross-linking reaction and so retained in situ for an extended period before the matrix degrades.

| Lane No. | Sample |
|---|---|
| 1 | 0 secs |
| 2 | 1 sec |
| 3 | 2 sec |
| 4 | 5 sec |
| 5 | 10 sec |
| 6 | 30 sec |
| 7 | 60 sec |
| 8 | Protein size standards |

Figure 4:
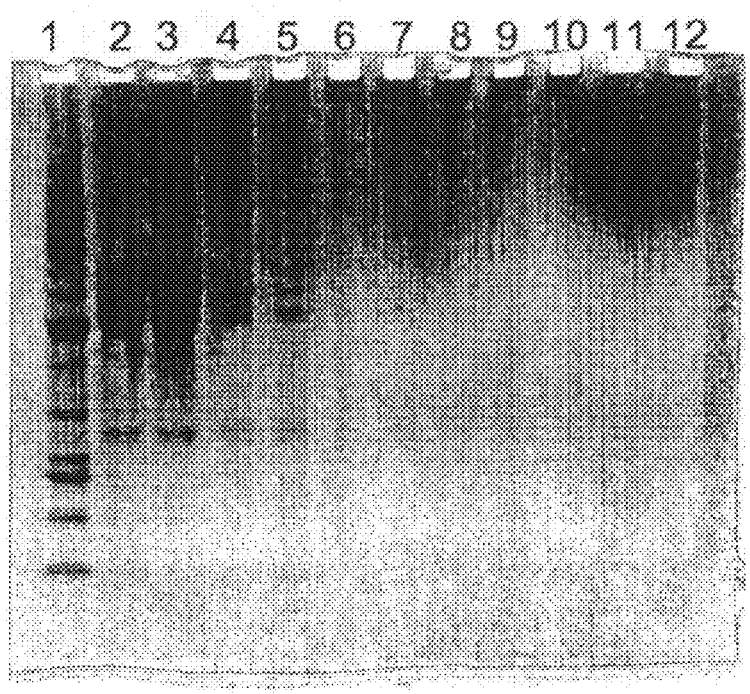

FIG. 4 shows a photograph of an electrophoresis gel in which reactions mixtures containing 25 μg of bovine fibrinogen (Sigma); 20 mM persulfate (Sodium salt) and various concentrations of [Ru(bpy)$_3$]Cl$_2$, all in 25 μl PBS, were exposed to 300 W incoherent light from Quartz Halogen dichroic source for 1 min.

| Lane No. | Sample |
|---|---|
| 1. | MW Standards (as above) |
| 2. | 2 mM [Ru(bpy)$_3$]Cl$_2$, No Light |
| 3. | 0 [Ru(bpy)$_3$]Cl$_2$ |
| 4. | 0 NaPS |
| 5. | 1 μM |
| 6. | 5 μM |
| 7. | 10 μM |
| 8. | 25 μM |
| 9. | 50 μM |
| 10. | 100 μM |
| 11. | 500 μM |
| 12. | 2000 μM |

Figure 5:
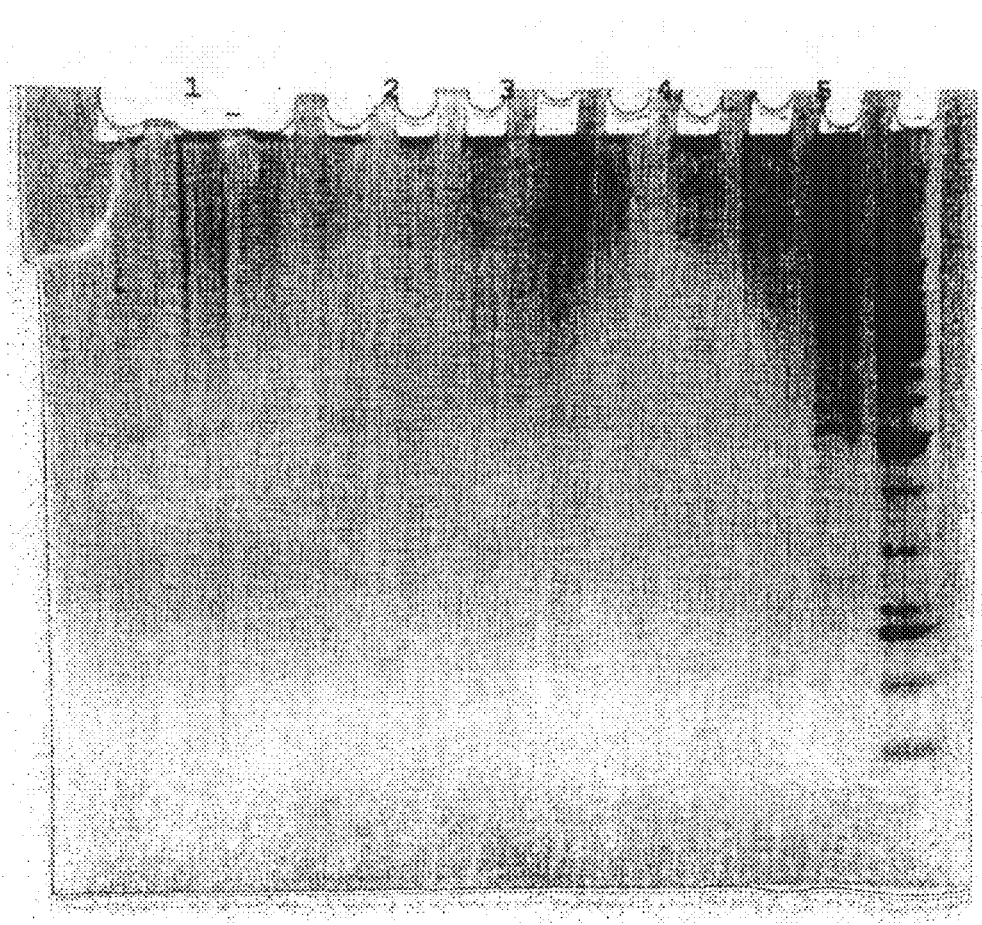

FIG. 5 shows a photograph of an electrophoresis gel in which reaction mixtures containing 25 μg of bovine fibrinogen (Sigma); 2 mM [Ru(bpy)$_3$]Cl$_2$ (Aldrich) all in 25 μl PBS. (SPS: sodium persulfate; APS: ammonium persulfate) were exposed to 300 W incoherent light from Quartz Halogen dichroic source for 1 min.

| Lane No. | Sample |
|---|---|
| 1. | 20 mM SPS |
| 2. | 10 mM SPS |
| 3. | 5 mM SPS |
| 4. | 2.5 mM SPS |
| 5. | 1.25 mM SPS |
| 6. | 0.63 mM SPS |
| 7. | 0.31 mM SPS |
| 8. | 10 mM APS |
| 9. | 2.5 mM APS |
| 10. | 0.63 mM APS |
| 11. | 0 persulfate |
| 12. | MW Standards. (as above) |

Figure 6:
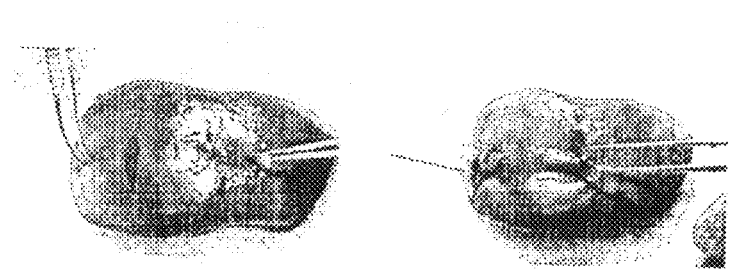

FIG. 6 is a photograph of a kidney (a) showing an incision and (b) with the incision sealed with a sealant according to the present invention.

Figure 7:
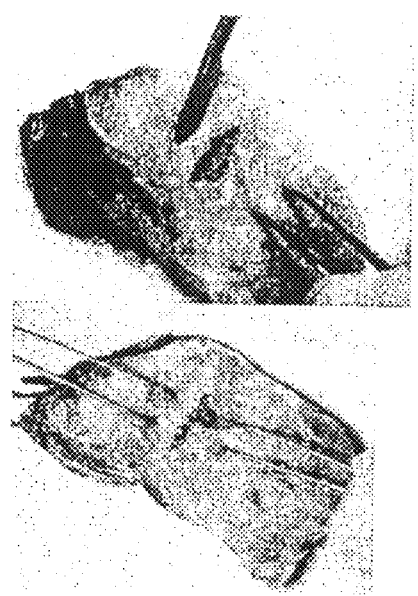

FIG. 7 is a photograph of a lung (a) showing an incision and (b) with the incision sealed with a sealant according to the present invention.

Figure 8:
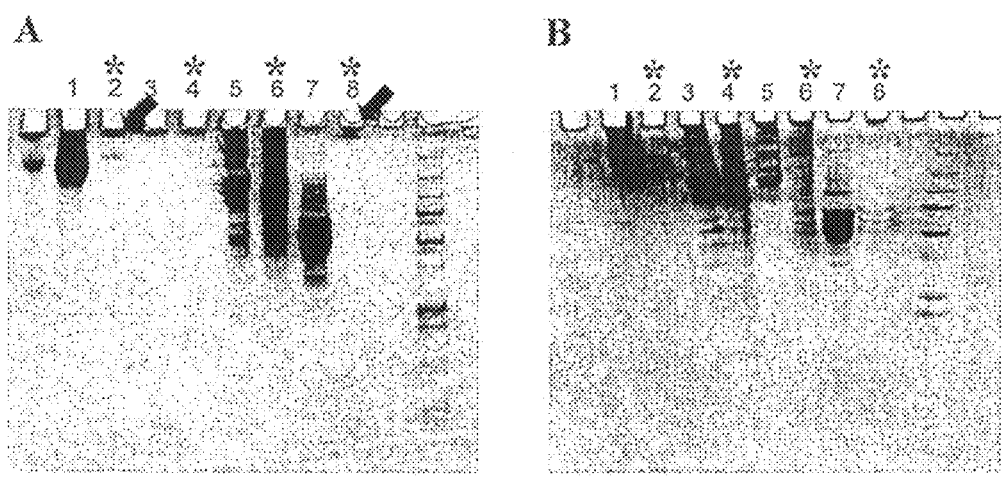

FIG. 8 shows a photograph of an electrophoresis gel that demonstrates ruthenium-catalysed photo-crosslinking of the additional matrix proteins fibronectin and collagen.
Lanes:
Gel A:
1. horse fibronectin
2. horse fibronectin crosslinked with [Ru(bpy)$_3$]Cl$_2$
5. Devro medical collagen (4 mg/ml); kangaroo tail
6. Devro medical collagen (4 mg/ml); kangaroo tail, cross-linked with [Ru(bpy)$_3$]Cl$_2$
7. bovine fibrinogen
8. bovine fibrinogen crosslinked with [Ru(bpy)$_3$]Cl$_2$
Gel B:
1. horse fibronectin
2. horse fibronectin crosslinked with [Ru(bpy)$_3$]Cl$_2$
3. Devro medical collagen (4 mg/ml); kangaroo tail
4. Devro medical collagen (4 mg/ml); kangaroo tail, cross-linked with [Ru(bpy)$_3$]Cl$_2$
5. Chicken collagen 6. Chicken collagen crosslinked with [Ru(bpy)$_3$]Cl$_2$
7. bovine fibrinogen
8. bovine fibrinogen crosslinked with [Ru(bpy)$_3$]Cl$_2$.

Figure 9:
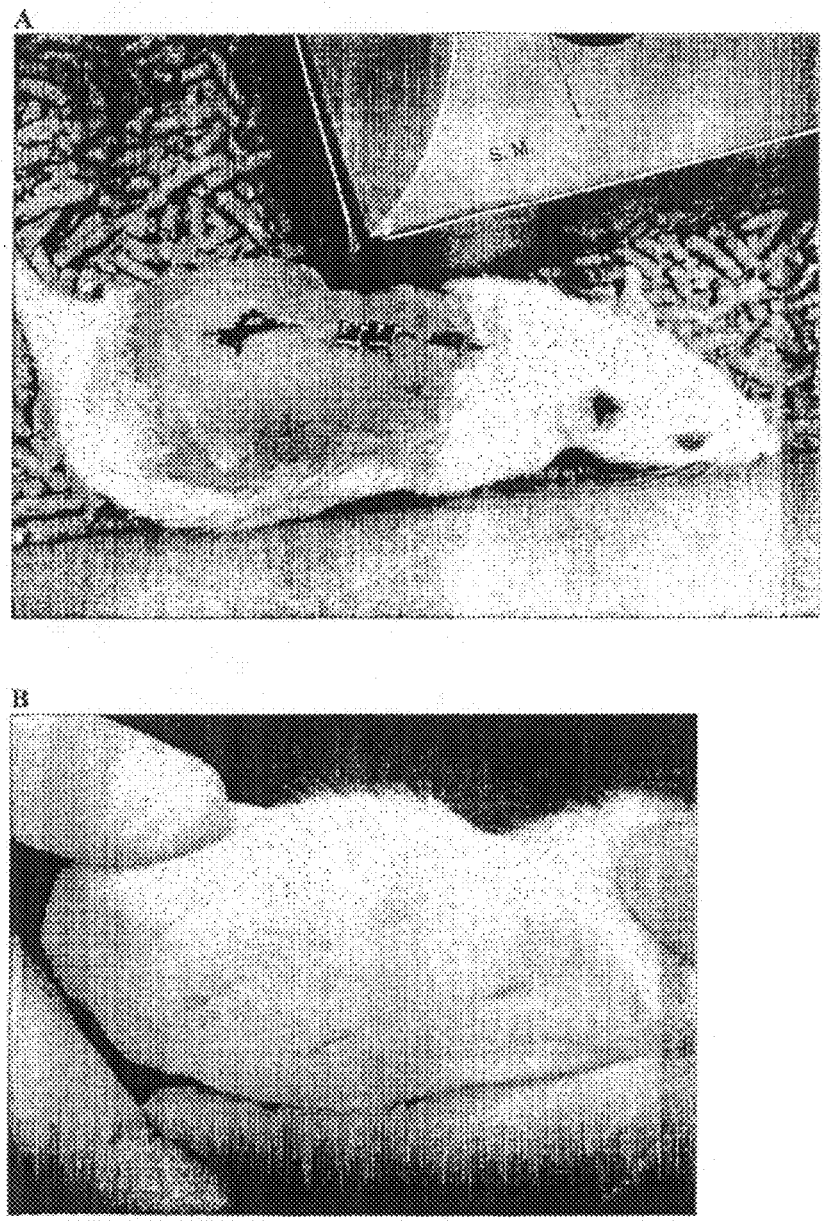
Figure 9:

FIG. 9 is a photograph of a rat (A) 2 hours after closure of three separate incisions (from head to tail) with (i) a fibrin glue (TISSEAL Duo 500) (ii) two 9 mm Mikron wound clips and (iii) fibrinogen-based tissue sealant in accordance with the present invention (B) 1 week after the operation and (C) 4 weeks after the operation as described in Example 9.

Figure 10:
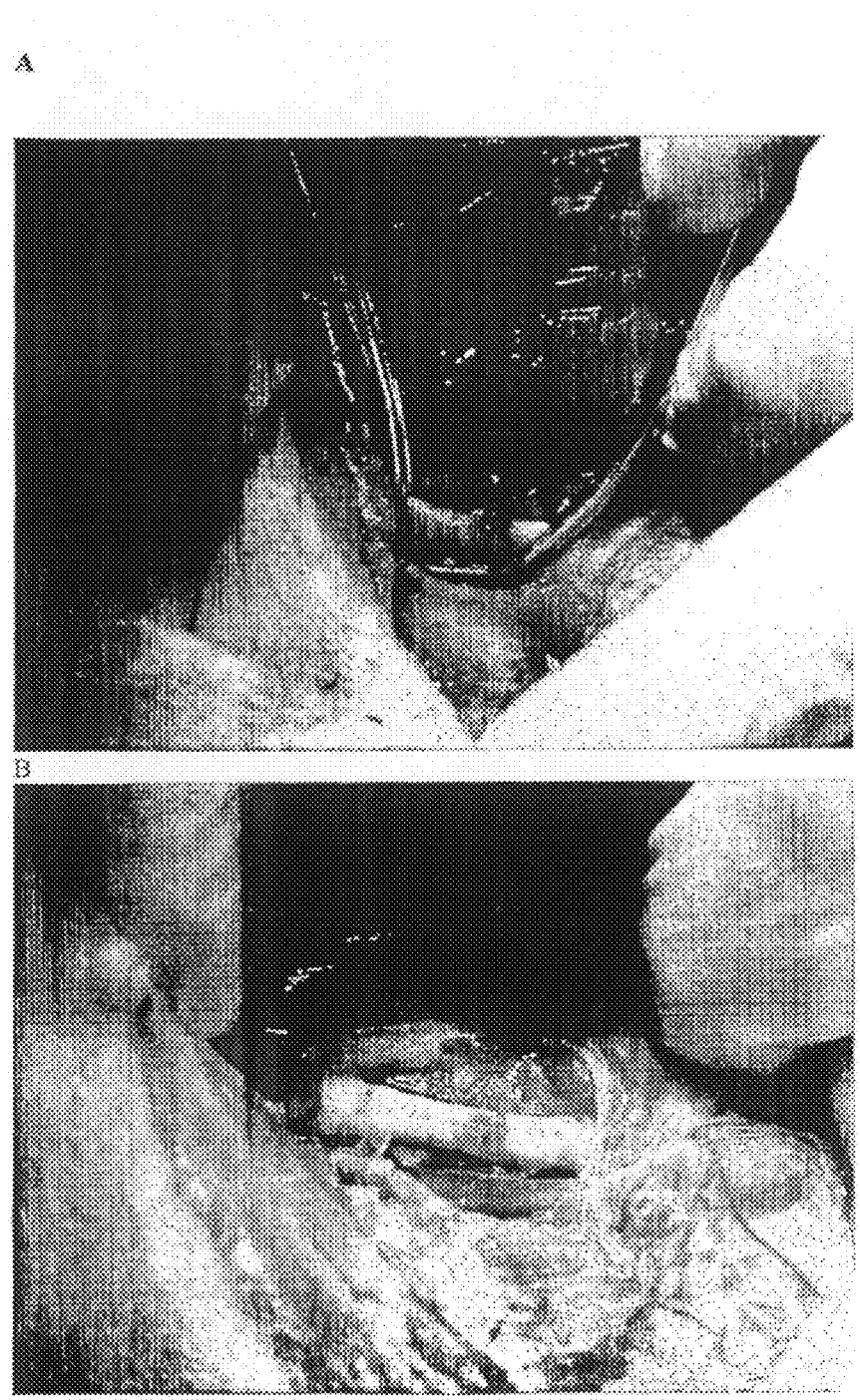
Figure 10:

FIG. 10 is a photograph showing application of fibrinogen-based tissue sealant in accordance with the invention to the left iliac artery in pigs: (A) applied with clamps at distal and proximal end of artery (B) clamps removed showing fully patent artery with good pulsatile flow and no leakage of blood and (C) 30 minute after application showing a complete patent artery with good pulsatile flow and no leakage of blood.

Figure 11:

FIG. 11 is a photograph showing a fibrinogen-based tissue sealant in accordance with the invention applied to an artery as a saturated solution on a piece of collagen/alginate dressing—fully patent artery with good pulsatile flow and no leakage of blood.

Figure 12:
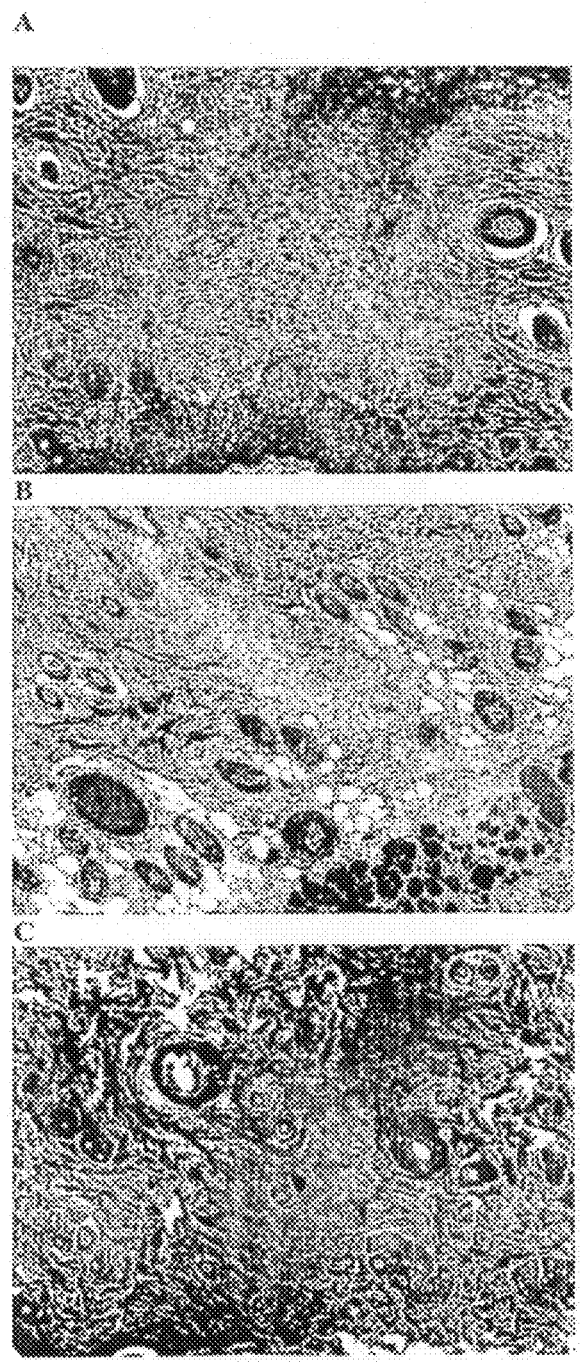

FIG. 12 is a photograph showing the time course of wound healing response using fibrinogen-based tissue sealant in accordance with the invention to treat skin incision in rats. Sections stained with Mason's trichrome. Explants from 1 week (A) show early signs of new collagen deposition (blue) within the incision zone. No indications of adverse foreign body giant cells or marked inflammatory responses. There were visible signs of new blood formation. Overall the 1 week explants show marked cellular infiltration into the wound. Explants from 2 weeks (B) indicate less cellurity and increased collagen deposition albeit the collagen bundles are thin indicating early healing. At 4 weeks, explants (C) show a more maturing wound healing response with markedly less cell infiltration and more signs of collagen deposition and re-modeling with signs of thicker collagen fibre bundles and follicular regeneration.

DETAILED DESCRIPTION OF THE INVENTION

The term "photoactivatable metal-ligand complex" as used herein means a metal-ligand complex in which the metal can enter an excited state when irradiated such that it can donate an electron to an electron acceptor in order to move to a higher oxidation state and thereafter extract an electron from an aromatic side chain, particularly tyrosine, of matrix protein to produce a free radical without reliance upon the formation of singlet oxygen. Suitable metals include but are not limited to Ru(II), Pd(II), Cu (II), Ni(II), Mn (II) and Fe (III) in the form of a complex which can absorb light in the visible region, for example, an Ru(II) bipyridyl complex, a Pd(II) porphyrin complex, a sulfonatophenyl Mn(II) complex or a Fe(III) protoporphyrin complex, more particularly, an Ru(II) bispyridyl complex or a Pd(II) porphyrin, in particular, an Ru(II)(bpy)$_3$ complex such as [Ru(II)(bpy)$_3$]Cl$_2$. Efficient cross-linking occurs in the presence of an electron acceptor such as a persulfate, more particularly, ammonium persulfate or sodium persulfate, and requires only moderate intensity visible light. Other possible electron acceptors include Co(III)(NH$_3$)$_5$Cl$^{2+}$; periodate, perbromate, perchlorate. The options and types of chemistry involved are outlined in Brown, K C and Kodadek, T *Met Ions Biol Syst*. 2001; 38:351-84. "Protein cross-linking mediated by metal ion complexes", the contents of which are incorporated herein by reference.

As used herein the term "electron acceptor" means any easily reduced molecule that will facilitate the cross-linking reaction.

As used herein the term "matrix protein" refers to isolated and purified forms of the proteins which are abundant and common in the extracellular matrix of animals. Typical matrix proteins are fibrinogen, fibrin, collagen, fibronectin, keratin and laminin, or admixtures thereof, and these may be isolated from human or animal sources or prepared, for example, using recombinant DNA technology. In addition, derivatives of these compounds or extracts containing them are suitable for use in the present invention, and they may be used in admixture.

As used herein the terms "fibrin" and "fibrinogen" encompass fibrin and fibrinogen themselves, purified fibrin or fibrinogen sub-units or composites or admixtures thereof. These might be isolated from human or animal whole blood or plasma. Alternatively these products or active homologs or fragments thereof may be prepared by genetic engineering, and such products are also envisaged for use in the present invention. For example, Pharming is developing three fibrinogen genes (rTS) under the transcriptional control of the bovine α S-casein promoter to achieve high level, mammary gland-specific expression. Nuclear transfer technology has been used to generate a number of transgenic cows that show expression levels of human fibrinogen in the milk at levels of 1-3 g/l.

The inventors have also demonstrated that clotted fibrin itself (produced by treatment of soluble fibrinogen with thrombin and insoluble in phosphate buffer) can be rendered soluble by, e.g. addition of 2% acetic acid or other means, and this can also subsequently be crosslinked using the method of the invention.

As used herein the term "soluble fibrin" refers to fibrin that has been prepared from fibrinogen by, for example, hydrolysis with thrombin, then rendered soluble by addition of a weak acid such as 2% acetic acid, a chemical chaotrope such as urea, or other means.

As used herein the term "applying" or "apply" or "application" refers to sequential application of the matrix protein, photoactivatable metal-ligand complex and the electron acceptor in any order or to application of compositions comprising any one or more of the matrix protein, photoactivatable metal-ligand complex and the electron acceptor. The matrix protein, photoactivatable metal-ligand complex and the electron acceptor or compositions containing them in admixture may be provided and administered in solid form such as a lyophilized powder or a plug of material or in liquid such as a solution or foam. Application may be by way of an applicator such as a single or multiple barrel applicator directly to a tissue portion, including into an incision or wound, with one or more spreading devices such as a spatula, via an aerosol device such as a spray can, by placement manually or with a surgical instrument of a plug or closure such as a bandage, gauze, cloth, tampon, membrane or sponge comprising these compounds, or any other way in which the matrix protein, photoactivatable metal-ligand complex and the electron acceptor or compositions containing them in admixture may be placed.

As used herein the term "tissue" refers to a plurality of cells located in close juxtaposition, be they alike in character or unlike, and so includes a tissue in the histological sense such as muscle tissue but also includes discrete structures such as the walls of a vessel like a blood vessel and the surface of an organ, including a raw, cut surface. The usage of the term should be read in conjunction with the intended uses described herein, and is not intended to limit the uses described.

It is envisaged that the method of the present invention will be used to augment or as a replacement for conventional surgical closures such as sutures and staple and existing tissue adhesives generally; however, it is likely to have particular application in certain fields and applications. In particular the method will find application in fields where tissue adhesives such as fibrin glue are already used such as in cardiothoracic surgery, cardiovascular surgery, thoracic surgery, hepatic and pancreatic surgery, neurosurgery, aesthetic surgery, endoscopic surgery, prevention of seroma formation, bone healing, liver biopsy and dentistry.

The effectiveness of a sealant on hemostatis in cardiothoracic surgery is important to the clinical outcome; successful local hemostatis reduces blood loss, operative time, and the need for resternotomy in these high risk patients. Bleeding after open-heart surgery is a great problem in cardiac surgery. Due to hemostatic abnormalities, reoperation to control prolonged bleeding may be necessary. Therefore a sealant superior at producing hemostatis compared with conventional topical agents, such as collagen-coated dressings is desirable.

The method of the present invention will also be useful for sealing air leaks from lung procedures (even as treatment for bronchopleural fistulas). Thoracic surgery frequently involves pulmonary resection and decortications. The consequences of such surgical intervention include haemorrhage and air leaks. Retrospective analyses indicate that bronchopleural fistulae occur in 2% to 3% of patients after pulmonary resection, followed by a mortality of 15% to 20%. These complications can be overcome by the use of sealants of the invention.

Raw cut surfaces of soft tissues such as liver and lung cannot be isolated and secured by conventional techniques such as suturing. The management of these surfaces is important for preventing intrapertoneal complications, such as infection, abscess formation, and sepsis which may lead to hemorrhage, bile leakage, and fluid accumulation. Moreover, bile fluid is a severe irritant to the peritoneum and the prevention of bile leakage using a fibrin sealant is highly desirable. Therefore the sealant of the present invention finds application as a tissue sealant in hepatobiliary surgery.

Fibrin glue is used for dural closure by neurosurgeons to prevent cerebrospinal fluid leakages. The management of cerebrospinal fluid (CSF) fistulae is important. Fibrin sealant has been used in neurosurgical procedures for the prevention of CSF leakage from fistulae, and the sealant of the present invention will find application in preventing CSF leakages Aesthetic surgeons in Europe have routinely used fibrin-based glues in place of sutures, which has enabled them to avoid the use of drains for patients undergoing facial cosmetic surgery. There are basically two advantages of avoiding the use of drains and dressings: the postsurgical time is reduced by not putting on and removing the usual bulky dressings, and swelling, hematoma formation is reduced. Tissue adhesives have been reported to decrease the incidences of postoperative hematomas and edema, enable painful suture removal to be avoided, and, in some cases, facilitate early recovery and greater patient satisfaction. Plastic surgeons especially use adhesives to control burn bleeding after debridement and as adjuncts in surgery necessitating flaps. Skin grafting is the simplest and most effective method used to resurface large burn wounds. The graft initially adheres to its new bed by a thin layer of fibrin and nourishment of the graft occurs by plasmatic imbibition. Further ingrowth of blood vessels and fibrous tissue from the wound results in permanent adherence of the graft to its recipient site known as graft "take." This process can be hindered by collection of blood between the graft and bed, by shearing and by infection. The face is highly vascular and diffuse bleeding is difficult to control following burn wound excision. Traditionally, to overcome the problem of hematoma, the grafts are meshed to enable any fluid collection to drain. Unfortunately meshing produces scarring which impairs the final cosmetic result. Careful suturing can minimize shearing, but takes time, may promote bleeding and also leaves scars. The sealant of the present invention has several advantages in the excision and skin grafting of facial burns as it provides good hemostasis and helps prevent hematoma formation, it minimizes the use of sutures, which save operating time, and it avoids further bleeding during passing of the sutures. Plastic surgeons are also utilizing fibrin glue for the management of wrinkles of the forehead and of the aging face, and the sealant of the present invention will also be useful in this application. The technique avoids the classic coronal incision, utilized for the browlifting, thus minimizing morbidity. The adhesive not only helps to secure the forehead and scalp flaps in place, but also works as a hemostatic agent, decreasing hematoma formation and bruising.

The collection of serous fluids after operations is a very threatening problem and should be prevented. It can cause significant morbidity and delayed recovery. It can appear after a mastectomy and axillary dissection, soft tissue dissection (abdominoplasty, breast reduction, facelift), and muscle harvesting. The complications include pain, wound infection, flap necrosis, and increased costs but wound healing can be improved with intraoperative sealant application.

Use of the tissue adhesive in bone repair should promote osteoblastic activity rather than retarding it. In contrast, cyanoacrylates cause adverse bone reaction. Their space occupying nature prevents or retards healing and their degradation products are harmful.

Liver biopsy is frequently necessary for candidate evaluation or histologic follow-up of transplanted livers. Although generally considered to be safe, it carries a risk of complications in up to 0.5% of cases; hemorrhage being the most important. Another option is the so-called plugged percutaneous liver biopsy (PPLB), which uses direct injection of a plugging material into the biopsy tract, and sealants of the present invention could be used.

In dentistry the use the use of tissue adhesives shows less propensity for infection or delayed healing compared to the use of silk sutures which can result in foreign body reaction, fistula formation and submental abcess formation.

Tissue adhesives of the present invention may also be used as wound dressings. Absorbable adhesive bandages can be directly used in the control of battlefield wounds, and immediate local control of bleeding can be achieved. A further application may be as a hemostatic dressing in the operating room which is used instead of a sponge.

It is also envisaged that the present invention will provide a vehicle for local administration of drugs. It has the ideal characteristics to play such a role. In the method of the invention the matrix protein is placed at the site of a tissue injury, and is ultimately broken down and replaced by healing tissue as part of the body's natural healing process. Thus it initially controls bleeding but remains firmly fixed in place until it is naturally biodegraded. Therefore it is capable of delivery chemotactic, growth promoting, and differentiation factors to induce both soft and hard tissue production or the innovation of undesirable proliferation. It may also used to deliver conventional pharmaceuticals in the form of antibiotics and chemotherapy drugs for prolonged periods.

A wide range of drugs can be incorporated into the matrix for local action and/or systemic release. In particular, antibiotics, chemotherapeutics, peptide hormones, cytokines, antibodies, cell cycle regulators, chemokines, growth factors and secreted proteins may be incorporated in the matrix. The antibiotics may be from the fluoroquinolone class aminoglycocides such as hygromycin B, kanamycin and streptomycin, antifungal antibiotics such as amphotericin B, cyclohexamide, and nystatin, antineoplastic antibiotics, including mitomycin C, puromycin, and streptozocin, antitubercular antibiotics, including rifampicin and capreomycin, lactam antibiotics such as amoxicillin and penicillin, macrolide antibiotics, including nystatin and brefelden A, peptide antibiotics, including echinomycin and gramicicdin, tetracyclines, chloramphenicol and tunicamycin. Exemplary cytokines include, but are not limited to, the interleukins, beta-interferon, alpha-interferon, gamma-interferon, angiostatin, thrombospondin, endostatin, METH-1, METH-2, GM-CSF, G-CSF, M-CSF, tumor necrosis factor (TNF), and bone morphogenetic proteins (BMPs). Chemokines generally act as chemoattractants to recruit effector cells to the site of chemokine expression. Therefore the chemokines can recruit immune system components to the site of treatment. Suitable chemokines include, but are not limited to, RANTES, MCAF, MIP1-alpha, MIP1-Beta, and IP-10. Suitable growth factors include, but are not limited to, TGF-α, TGF-β, EGF, PDGF, FGFs, NGF, VEGF and KGF. Suitable secreted proteins include, but are not limited to, blood factors such as Factor VIII, Factor IX, von Willebrand Factor, and the like. Anti-cancer drugs have been demonstrated to show sustained release from a fibrin glue (Yoshida et al., 2000). Fibrin glues may also provide a slow release formulation for antibiotics when used in ocular surgery (Maronea et al., 1999). Furthermore fibrin glues have included antibiotics such as amikacin to prevent local graft infection (Nishimotol et al., 2004).

For the purposes of this specification it will be clearly understood that the word "comprising" means "including but not limited to", and that the word "comprises" has a corresponding meaning.

Comparative Example 1

Use of TISSEEL VH Fibrin Sealant

TISSEEL VH Fibrin Sealant contains the following substances in four separate vials:
1. Sealer Protein Concentrate (Human), Vapor Heated, freeze-dried
2. Fibrinolysis Inhibitor Solution (Bovine)
3. Thrombin (Human), Vapor-Heated, freeze-dried
4. Calcium Chloride Solution Freeze-dried Sealer Protein Concentrate and Thrombin are reconstituted in Fibrinolysis Inhibitor Solution and Calcium Chloride Solution respectively. The resulting Sealer Protein Solution and Thrombin Solution are then combined by using the Duploject System to form the Fibrin Sealant. The sterile Duploject System consists of a clip for two identical disposable syringes and a common plunger which ensures that equal volumes of the two components are fed through a common joining piece before being mixed in the application needle and ejected. After the two components have been applied, the sealed parts are fixed or held in the desired position for at least three to five minutes to ensure that the setting TISSEEL VH Fibrin Sealant adheres firmly to the surrounding tissue. Solidified TISSEEL VH Fibrin Sealant reaches its ultimate strength after about two hours (70% after about 10 minutes). Thus the process suffers from unacceptably long cure times for many applications.

Comparative Example 2

Use of PEG Copolymer (FOCALSEAL-L) as a Tissue Sealant

Diagnosis of lung cancer often requires that patients have lung tumors surgically removed. After tumors are removed, air leaks can develop around the sutures or staples used in the surgical procedure. Air leaks may be closed by suturing, stapling tissue, or applying surgical mesh over the air leak or using FOCALSEAL, which is a polyethylene glycol (PEG) sealant. The PEG does not adhere to tissue, but rather forms a "plug" with the opening to the lung which seals the leak. The application of FOCAL SEAL is a two-step process involving application of a primer layer and then a PEG layer to the lung tissue by "painting" the lung surface. Once coated, the lung tissue is irradiated for 30 or 40 seconds. 39% of patients treated with FocalSeal-L Sealant and standard surgical closure techniques were air-leak free when they were discharged from the hospital compared to 11% percent of patients treated with standard techniques alone. The studies also showed that the amount of time required to stop air leaks was less than with standard techniques. Side effects were about the same although the patients treated with FocalSeal-L Sealant had a somewhat higher rate of infection (7.2% vs. 3.6%). Thus, while it is a photochemical process with a rapid cure it involves a two-step application, and the PEG-based plug does not bind the adjoining tissue.

Example 1

Photochemical Cross-Linking of Bovine Fibrinogen

Figure 1:
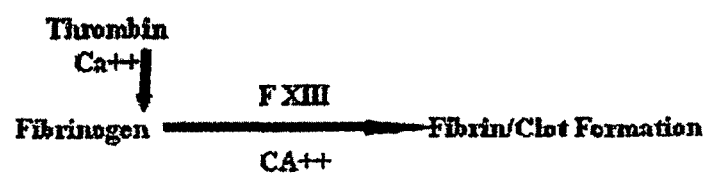
FIG. 1 is a diagram illustrating the mechanism of action of fibrin glues.
Figure 2:
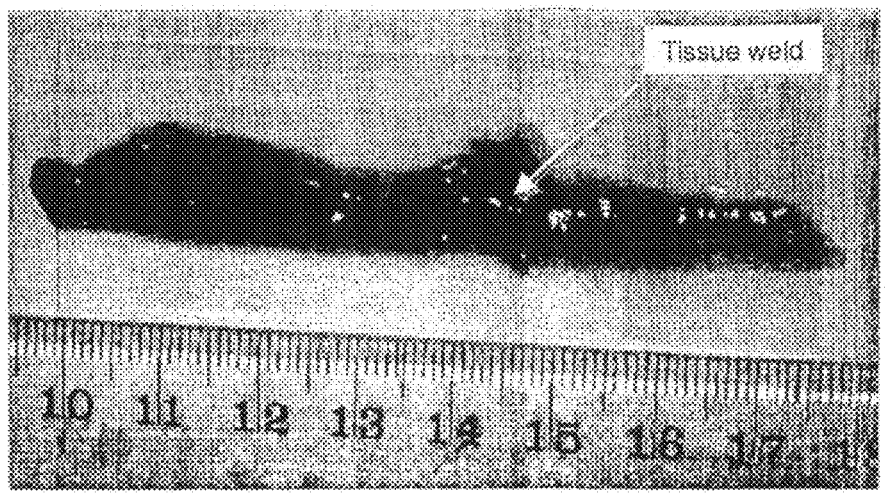
FIG. 2 is a photograph which illustrates the tissue adhesive properties of the present invention. The photograph shows two small strips of bovine longissimus dorsi (LD) which have been attached by coating opposing surfaces coated in a sealant solution in accordance with the present invention (200 mg/ml bovine fibrinogen was dissolved in PBS, with 2 mM [Ru(bpy)$_3$]Cl$_2$, 10 mM ammonium persulfate). Following 10 sec of irradiation, the two pieces of muscle were firmly attached at the position shown by the arrow in the photograph.

A photochemical method was used to cross-link the soluble fibrinogen into a solid biomaterial and to effect the covalent cross-linking of the fibrinogen matrix to the proteins contained in the extracellular matrix surrounding the muscle tissue. Two small strips of bovine longissimus dorsi (LD) were dissected and the opposing surfaces coated in the sealant solution (200 mg/ml bovine fibrinogen was dissolved in PBS, with 2 mM [Ru(bpy)$_3$]Cl$_2$, 10 mM ammonium persulfate). Following 10 sec of irradiation, the two pieces of muscle were firmly attached at the position shown in FIG. 2. The light source chosen for the present study was a 600-W tungsten-halide source (2×300-W lamps; GE #38476). The spectral output showed a broad peak from 300 nm-1200 nm. Bovine fibrinogen (Fraction I, Sigma) (200 mg/ml) was dissolved in PBS, with 2 mM [Ru(bpy)$_3$]Cl$_2$, 10 mM ammonium persulfate) and photochemically cross-linked (600 W at 10 cm for 10 s).

Example 2

Degradation of and Tissue Response to Polymerised Fibrinogen Biopolymers In Vivo The solid fibrinogen biomaterial to be evaluated in the rat subcutaneous implant study is derived from a purified soluble fibrinogen protein which was crosslinked using a photochemical method involving Tris(bipyridyl) Ruthenium (II) chloride (2 mM final concentration) and ammonium persulphate (20 mM final concentration). The light source chosen for these studies was a 600-W tungsten-halide source (2×300-W lamps; GE #38476). The spectral output showed a broad peak from 300 nm-1200 nm. Preliminary in vitro cytotoxicity evaluations on this purified expressed protein biomaterial had been encouraging however further, standard cell culture methods to screen for direct and leachable potential toxic components were required prior to implantation in animals. Therefore the fibrinogen biomaterials were evaluated in rats for tissue responses as well as the extent of degradation of the material over a 36 week period (3, 8, 18 and 36 weeks).

Method

Animals 40, female, 8 week old, Wistar rats were purchased from the Animal Resource Centre, Canning Vale Wash. The rats were allowed to acclimatise to their new surroundings for 2 weeks prior to implantation of fibrinogen samples.

Anaesthesia

Isoflurane, gaseous anaesthetic was used as the anaesthetic of choice because it has rapid induction and fast recovery. Each rat was induced with isoflurane (5%) in a mixture of oxygen (2 liters/minute). Induction of anaesthesia took approximately 30-60 seconds. Once the concentration of Isoflurane was reduced to 2% in a mixture of oxygen (2 liters/minute).

Subcutaneous Implantation

The dorsum of the rat was shaved with clippers and the skin was disinfected with Iodine surgical scrub. A small incision was then made (approx 7 mm) through the dermis to the muscle layer. A pocket then created by parting the connective tissue between the dermis and muscle layer using blunt/blunt scissors. The sample plug was then gently placed in the pocket and positioned away from the initial incision point. The wound was closed using 2 9 mm wound clips. Groups 2, 4 & 5 had 2 subcutaneous biopolymers implanted per rat, each in a separate pocket. Group 3 only one biopolymer was implanted.

The samples implanted are as follows (suspended in PBS+protease inhibitor cocktail):
1) Fibrinogen (Sigma fraction I) (crosslinked using photochemical method—the product is applied as a composition comprising fibrinogen, the Ru(II) catalyst and ammonium or sodium persulfate referred to hereinafter as "Fibrinogen-based Tissue Sealant" or "FBTS" and then irradiated)

Each plug (100 µl of 200 mg/ml) of cross-linked fibrinogen was conical in shape: 4 mm on base, 1 mm at top and 5-6 mm high. All plugs were beige/brown in colour.

The height (width) and length of each polymer was measured using digital callipers weekly for the first 4 weeks and then every 2 weeks for the remainder of the experiment.

One week after implantation of the fibrinogen samples no swelling was observed (except one rat where the wound is most likely infected). All animals seem normal in behaviour and appearance.

Two weeks after implantation all plugs that had increased in size were similar in size to that implanted or had slightly reduced. No inflammation was observed.

Three weeks after implantation 2 rats from each group were killed First time point: No gross pathology was noted in any organ and all organs (heart, liver, spleen, lung and kidney) were all histologically normal. Most plugs appeared to have started to degrade/be reabsorbed. Most had a thin capsule covering the plug. The fibrinogen plugs were flattened. No macroscopic/gross inflammation was noted at any of the implantation sites or around any of the plugs.

Eight weeks Second time point 2 rats were killed from each group. The fibrinogen plugs had reduced in size and were spherical in shape. One animal from the fibrinogen group had hardened kidneys with an enlarged spleen—possible carcinoma of the kidneys, however this was unrelated to the implant.

Eighteen weeks Third timepoint. 2 rats from each group were killed. No plugs were seen in animals implanted Fibrinogen. The plugs had fully degraded/been reabsorbed. There was no gross pathology seen in any of the major organs from all animals.

Thirty six week—Study Terminated. The study was terminated. The implanted plugs from all groups had fully degraded or been reabsorbed. No gross pathology was noted in any of the major organs from any animal.

Example 3

Strength of Fibrinogen-Based Tissue Sealant (FBTS)

The comparative strength of tissues joined using FBTS and tissues joined using fibrin glue was measured using de-fleeced adult sheep skin. Skin was de-haired and the dermal surface scraped clean using a wire brush. The skin was soaked in phosphate-buffered saline (PBS) and "dumbbells" (ca. 10 cm×1 cm) were cut from the re-hydrated skin for tensile testing. An incision was made across the width of a dumbbell shaped strip of skin, and the two halves then "glued" or sealed (at room temperature) following photochemical treatment of fibrinogen in accordance with the present invention. The adhesive properties of FBTS was compared with a commercial fibrin-based tissue sealant (Tisseel™-Baxter), used as instructed by the manufacturer. The glued skin was then mounted in a tensile testing instrument (Instron) and tested for load to break. The units are Newtons (N). The cut dumbbells were either overlapped by 1 cm at the join or were butt-joined with both tissue sealants.

The cross-linked fibrinogen was prepared using a fibrinogen concentration of 100 mg/ml, 150 mg/ml or 200 mg/ml and samples were irradiated for 60 seconds using a 300 W tungsten-halide lamp at 15 cm from the surface. Tisseel™ was applied (according to the manufacturer's instructions) to the cut surfaces and these were held together and allowed to cure for 5 minutes, 20 minutes or 80 minutes prior to tensile testing.

Explanation of Samples Described in Table 1:

FB=sigma bovine fibrinogen used at 5 concentrations as described. Overlapped sections sealed with FBTS, which was applied to the dermal surface between overlapping sections, which were gently pressed together. Each side was irradiated for 60 seconds.

Tisseel was tested in the same way. Bonds were allowed to set for 5 min to 80 minutes prior to testing, as described.

Collagen=Devro medical collagen 4.1 mg/ml with [Ru(bpy)$_3$]Cl$_2$ and persulphate as per FBTS.

"FB 75/collagen 75" describes a 1:1 mixture of 150 mg/ml fibrinogen and 4.1 mg/ml Devro collagen.

"FB 60/collagen 60" describes a mixture of 150 mg/ml fibrinogen and 20 mg/ml purified bovine collagen (type 1).

TABLE 1

Summary of Physical Testing
Cros-head speed 50 mm/min

| | Max Load (N) | | | | |
| --- | --- | --- | --- | --- | --- |
| | Sample | | | | |
| | Sample 1 | Sample 2 | Sample 3 | Mean | Std Dev |
| FB 100 mg/ml overlap (60 sec × 2 sides) | 0.83 | 1.84 | 2.27 | 1.65 | 0.74 |
| FB 150 mg/ml overlap (60 sec × 2 sides) | 1.75 | 1.58 | 2.54 | 1.96 | 0.51 |
| FB 200 mg/ml overlap (60 sec × 2 sides) | 4.65 | 2.93 | 1.80 | 3.13 | 1.44 |
| Collagen 4.1 mg/ml overlap (60 sec × 2 sides) | 0.62 | 0.40 | | 0.51 | 0.16 |
| Tisseel overlap 80 min | 0.56 | 1.29 | 1.32 | 1.06 | 0.43 |
| Tisseel overlap 20 min | 0.16 | 0.79 | 0.30 | 0.42 | 0.33 |
| Tisseel overlap 5 min | 0.47 | 1.13 | 1.10 | 0.90 | 0.37 |
| FB 165 mg/ml overlap (60 sec × 2 sides) | 2.85 | 4.38 | 3.04 | 3.42 | 0.83 |
| FB 75 mg/ml overlap (60 sec × 2 sides) | 0.98 | 0.83 | | 0.91 | 0.11 |
| FB 60/collagen overlap (60 sec × 2 sides) | 4.00 | 3.92 | 2.28 | 3.40 | 0.97 |
| FB 75/collagen overlap (60 sec × 2 sides) | 1.23 | 0.34 | 0.35 | 0.64 | 0.51 |
| Tisseel butt 80 min | 0.32 | 0.59 | 0.26 | 0.39 | 0.18 |
| Tisseel butt 20 min | 0.25 | 0.15 | 0.25 | 0.22 | 0.06 |
| Tisseel butt 5 min | 0.27 | 0.32 | 0.41 | 0.33 | 0.07 |
| FB 165 mg/ml butt (60 sec × 2 sides) | 0.58 | 0.52 | 0.57 | 0.56 | 0.03 |

Results

The results show that the FBTS product produces 2- to 3-fold stronger tissue bond than the fibrin-based product Tisseel ™ in both overlap and butt-joints. Furthermore, FBTS acts more rapidly to achieve maximum bond strength.

Example 4

Time of Light Exposure

Reactions contained 25 μg of bovine fibrinogen (Sigma); 2 mM [Ru(bpy)$_3$]Cl$_2$; 20 mM persulfate (Sodium salt) all in 25 μl PBS.

Figure 3:
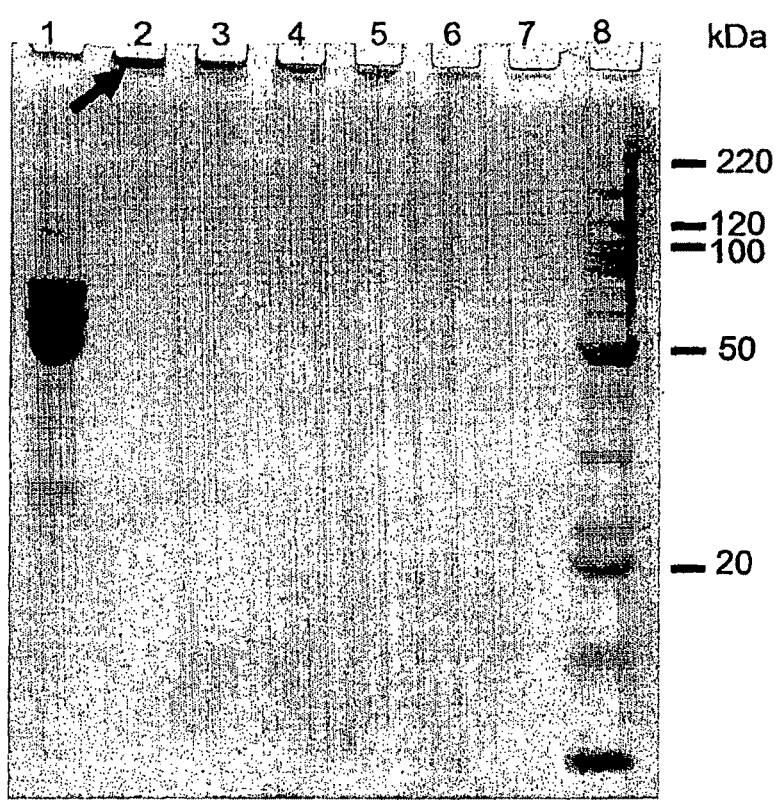
FIG. 3 shows a photograph of electrophoresis gel in which reaction mixtures containing 25 μg of bovine fibrinogen (Sigma); 2 mM [Ru(bpy)$_3$]Cl$_2$; 20 mM persulfate (Sodium salt) all in 25 μl PBS were exposed to 300 W incoherent light from Quartz Halogen dichroic source for various times.

Reactions were exposed to 300 W incoherent light from Quartz Halogen dichroic source for 1, 2, 5, 10, 30 and 60 seconds all resulted in the formation of high molecular weight, cross-linked fibrinogen polymers (FIG. 3).

Example 5

Effect of Concentration of [Ru(bpy)$_3$]Cl$_2$

Reactions contained 25 μg of bovine fibrinogen (Sigma); 20 mM persulfate (Sodium salt) all in 25 μl PBS. Reactions were exposed to 300 W incoherent light from Quartz Halogen dichroic source for 1 min (FIG. 4) showing that the cross-linking reaction occurs across a range of [Ru(bpy)$_3$]Cl$_2$ concentrations.

Example 6

Effect of Concentration of Persulfate

Reactions contained 25 μg of bovine fibrinogen (Sigma); 2 mM [Ru(bpy)$_3$]Cl$_2$ (Aldrich) all in 25 μl PBS. (SPS: sodium persulfate; APS: ammonium persulfate).

Reactions were exposed to 300 W incoherent light from Quartz Halogen dichroic source for 1 min (FIG. 5) demonstrating efficacy across a range of concentrations.

Example 7

Preliminary testing involved the examination of the sealant properties of FBTS using porcine fibrinogen to repair incisions made in abattoir specimens of various bovine tissues (see FIGS. 6 and 7). These appeared to form rather strong tissue welds, as in some cases the surrounding tissue was ruptured in attempting to disrupt the tissue seal.

Example 8

This example demonstrates an in vivo application of a simple skin incision wound model through comparison of formulations of the product of the invention with standard wound clips and commercial glue.

Materials & Method:

Animals: 20, Sprague Dawley, 8 week old, female rats were purchased from Animal Resource Centre, Canning Vale, Wash. (Two lots of 10 rats). The rats were approx 190 g in weight. Prior to surgery the rats were housed in groups of 5 and allowed to acclimatize for 7 days.

Anaesthesia: At the time of surgery rats were anaesthetized with 150 μl/100 g body weight ip injection of ketamine and xylazine mixture. (3 ml ketamine (50 mg/ml) added to 0.75 ml Xylazine (20 mg/ml)). This provided a sleep time of 2 hrs and an anaesthetic time of 20 mins.

FBTS Product—

A working solution containing 150 mg/ml fibrinogen, 2 mM [Ru(bpy)$_3$]Cl$_2$, 20 mM sodium persulfate, 100 μg/ml streptomycin and 1000 units penicillin was prepared.

Surgery:

Once a surgical plane of anaesthesia was established the rat dorsum was shaved and the skin disinfected with an Iodine Surgical Skin Preparation. Three 1.5 cm incisions were made along the rats dorsum through the dermal layer to the underlying muscle layer. Each incision was closed with one of 3 methods (see Table 2 for closure plan):

1. 9 mm MikRon Autoclip Wound Clips (from Becton Dickerson lot number 11003497G)—wound clips were then removed 5-7 days post surgery
2. Tisseel Duo 500™—Two component fibrin sealant made by Baxter A G, Vienna, Austria.
3. FBTS (in accordance with the present invention)

The wounds were monitored daily for the first 7 days and twice a week for the remainder of the study.

Results:

2 hrs post surgery: All rats recovered well form anaesthetic. All wound closures look good and there was no bleeding from any closure.

24 hrs post surgery: All rats are alert and recovered well. All closures look good. There is little difference between Tisseel or FBTS method of closure.

2 days Post Surgery: All closures look good. No scab formation suggesting that both Tisseel and FBTS have prevented blood flow and sealed the wound. There was no inflammation noted at any surgical site. There is no difference between closure methods of Tisseel or FBTS. Wound clips provided good knitting between the edges of the incision where as with the other methods a small gap was noted in some of the rat closures.

6 days Post Surgery: Wound clips were removed from all rats. All incision wounds healed exceptionally well. There was no inflammation or irritation around any incision site. The rats were alert and not in any pain. Rats had increased in weight to approx 240 g.

28 Days Post Surgery: All rats were well. The fur had grown back across the incision sites.

Example 9

Histology of FBTS implants in rats. Comparison with Tisseel Duo 500 and a wound clip closure.

The dorsal side of the rat was shaved and the skin disinfected with surgical iodine. Once a surgical plane of anesthesia was reached, three 1.5 cm incisions were made on the dorsum down the midline. One incision was closed with two 9 mm Mikron wound clips. Another was closed by applying commercial wound glue (Tisseel Duo 500) and the third was closed by applying FBTS to the wound. The light source chosen for these studies was a 600-W tungsten-halide source (2×300-W lamps; GE #38476). FBTS comprised bovine fibrinogen (Fraction I, Sigma) (165 mg/ml) dissolved in PBS, and this was used with 2 mM [Ru(bpy)$_3$]Cl$_2$, 20 mM sodium persulfate) and photochemically crosslinked (600 W at 10 cm for 30 s).

The area around the wounds was dressed with a sterile wound dressing and the area taped to prevent the animals from pulling at the wounds. This was removed 48 hrs after surgery. The wounds were monitored daily for the first 7 days and twice a week for the remainder of the study. At 1, 2, 4 and 7 weeks post surgery 5 animals were killed with sodium pentobarbital. Photographs showing the progress of the wounds as they heal are seen in FIG. 9. The skin around the 3 wounds was excised and samples were excised for mechanical tensile testing (Table 2), gross vascularity (visual inspection for vascular development) and a full histological analysis including Haematoxylin and eosin (H&E) and Mason's trichrome staining. The dimensions of the dumbbell-shaped sample prepared for mechanical testing was 3 cm×0.7 cm. (at the midpoint).

TABLE 2

Maximum strength of healed wounds in rat skin - recovery after wounding.

| | Load at max (N) Treatment | | | |
|---|---|---|---|---|
| Sample date | Tisseel | Wound clip | FBTS | Control* |
| 1 week | 5.9 | 12.0 | 5.7 | 46.9 |
| 2 weeks | 3.6 | 2.5 | 4.1 | 46.9 |
| 4 weeks | 25.8 | 16.4 | 28.9 | 46.9 |
| 7 weeks | 53.5 | 34.8 | 55.6 | 46.9 |

*Control values are the mean of 6 animals measured on surgically untreated skin.

The summaries below are reports of wound healing histology at 1 week, and 4 weeks post wound healing.

1 Week Samples: FBTS

Low magnification of 1 week sample: H and E staining showed good cellular infiltration within the fibrinogen FBTS, and Mason's trichrome showed early signs of new collagen deposition (stained blue) within the incision zone. No indications of adverse foreign body giant cells or marked inflammatory responses.

High magnification of 1 week FBTS, Mason's trichrome staining showed good cellular infiltration (stained mauve colour) accompanied by deposition of new small collagen fibre bundles. In addition, there are visible signs of vascularisation.

1 Week Samples: Tisseel Duo 500

Low magnification of 1 week sample: H and E staining showed good cellular infiltration within the Tisseel, and Masson' trichrome showed early signs of new collagen deposition (blue) within the incision zone with more intense inflammation in the deeper region of the incision.

High magnification of 1 week Tisseel, Mason's trichrome staining showed good mixed cellular infiltration (mauve) accompanied by deposition of new small collagen fibre bundles. In addition, there were visible signs of foreign body giant cells and quite an intense inflammation.

1 Week Samples: Wound Clip Closure

Low magnification of 1 week sample: H and E staining showed good cellular infiltration within the incision, and Masson' trichrome showed early signs of some new collagen deposition (blue) within the incision zone 4 Week Samples: FBTS Low and high magnification of 4 week explant of FBTS, Mason's trichrome staining, showed less cellular infiltration compared with 1 week explants and more pronounced new matrix (collagen) deposition. Collagen bundles appear thicker than 1 week and there were also indications of follicular regeneration in the incision wound.

4 Week Samples: Tisseel Duo 500

Low and high magnification of 4 week explant of Tisseel, Mason's trichrome staining, showed less cellular infiltration compared with 1 week explants and more pronounced new matrix (collagen) deposition. Collagen bundles appeared thicker than 1 week and there were also indications of follicular regeneration in the incision wound.

4 Week Samples: Wound Clip Closure

Low and high magnification of 4 week explant of Wound clip closure alone, Mason's trichrome staining, showed persisting mild cellular infiltration compared with FBTS and Tisseel explants and pronounced new matrix (collagen) deposition. Collagen bundles appeared thicker than 1 week and there were also indications of some follicular regeneration in the incision wound.

FBTS Wound Healing: Sealing Skin Incision in Rats (Summary Up to 4 Weeks)

Time course of wound healing response using FBTS to treat skin incision in rats. Sections stained with Mason's trichrome (FIG. 12). Explants from 1 week showed early signs of new collagen deposition (blue) within the incision zone. No indications of adverse foreign body giant cells or marked inflammatory responses. There were visible signs of new blood formation. Overall the 1 week explants showed marked cellular infiltration into the wound. Explants from 2 weeks indicated less cellularity and increased collagen deposition albeit the collagen bundles were thin indicating early healing. At 4 weeks, explants showed a more maturing wound healing response with markedly less cell infiltration and more signs of collagen deposition and re-modeling with signs of thicker collagen fibre bundles and follicular regeneration.

Example 10

Haemostat properties of fibrinogen-based tissue sealant (FBTS) in a surgical pig model.

These experiments exemplify both haemostasis in a live animal model (major arteries) using FBTS and also the use of a collagen matrix as a reinforcement support.

A piglet was anaesthetised under general anaesthetic and its internal organs surgically exposed. The animal was ventilated. A number of major arteries were punctured with an 18G needle, clamps applied to the distal and proximal sides of the puncture wound, the site was swabbed and FBTS applied. Light (irradiation time varied from 30 seconds to 5 seconds) from a 300 W xenon endoscope source was used to effect the photochemical reaction, using fibrinogen at 150 mg/ml, [Ru(bpy)$_3$]Cl$_2$ at 2 mM and sodium persulphate at 20 mM. Nominally, 100 μl was applied using an automatic pipette fitted with a 1 ml disposable tip, the end of which was cut off to facilitate liquid flow. FBTS was either used alone as a liquid, or applied to a collagen/alginate fabric (Fibracol collagen-alginate wound dressing from J&J Medical) to effect haemostasis.

FBTS Applied to Common Left Iliac Artery in Pigs.

Iliac artery was punctured with an 18G needle. Blood flow was stemmed using surgical clamps applied proximally and distally to the perforation, FBTS was applied using a pipette and cured for 20 seconds using light as described (FIG. 10).

The proximal clamp was removed first, allowing pressure to build and providing confirmation that the seal was patent. The distal clamp was removed and normal blood flow was returned with good pulsatile flow and no leakage of blood.

30 minute after FBTS application, the seal remained patent and normal arterial blood flow was observed. There was good pulsatile flow and no leakage of blood.

FBTS Applied to Left Renal Artery in Pigs.

The left renal artery was punctured with an 18G needle. Blood flow was stemmed using surgical clamps applied proximally and distally to the perforation, FBTS was applied using a pipette and cured for 20 seconds using light as described.

The proximal clamp was removed first, allowing pressure to build and providing confirmation that the seal was patent. The distal clamp was removed and normal blood flow was returned with good pulsatile flow and no leakage of blood.

30 minute after FBTS application, the seal remained patent and normal arterial blood flow was observed. There was good pulsatile flow and no leakage of blood.

FBTS Applied to Descending Aorta.

The descending aorta adjacent to the branch of the left renal artery, was punctured with an 18G needle. Blood flow was stemmed using surgical clamps applied proximally and distally to the perforation, FBTS was applied using a pipette and cured for 20 seconds using light as described.

The proximal clamp was removed first, allowing pressure to build and providing confirmation that the seal was patent. The distal clamp was removed and normal blood flow was returned with good pulsatile flow and no leakage of blood.

30 minute after FBTS application, the seal remained patent and normal arterial blood flow was observed. There was good pulsatile flow and no leakage of blood.

FBTS Applied in Conjunction with a Collagen Patch Applied to Descending Aorta.

The trial was repeated as above but including a 7 mm×7 mm patch of Fibracol™ collagen-alginate wound dressing, which was saturated with FBTS by immersion and held at the wound site with forceps up to application of light.

The descending aorta distal to the left renal artery was punctured with an 18G needle. Blood flow was stemmed using surgical clamps applied proximally and distally to the perforation. The FBTS-soaked patch was applied as described and cured for 20 seconds using light.

The proximal clamp was removed first, allowing pressure to build and providing confirmation that the seal was patent. The distal clamp was removed and normal blood flow was returned with good pulsatile flow and no leakage of blood.

30 minute after FBTS application, the seal remained patent and normal arterial blood flow was observed. There was good pulsatile flow and no leakage of blood.

FBTS Treatment with 5 Second Light Illumination.

The above example on the descending aorta was repeated exactly as described with FBTS liquid alone. The xenon light source was applied for 5 seconds then shut off prior to removal of the surgical clamps as described.

The proximal clamp was removed first, allowing pressure to build and providing confirmation that the seal was patent. The distal clamp was removed and normal blood flow was returned with good pulsatile flow and no leakage of blood.

REFERENCES

The disclosure of the following documents is incorporated herein by reference:

Brown, K C and Kodadek, T *Met Ions Biol Syst.* 2001; 38:351-84. "Protein cross-linking mediated by metal ion complexes"

Dickneite, G., H. J. Metzner, M. Kroez, et al. "The Importance of Factor XIII as a Component of Fibrin Sealants." *Journal of Surgical Research* 107 (October 2002): 186-195.

Dodd, R. A., R. Cornwell, N. E. Holm, et al. "The Vivostat Application System: A Comparison with Conventional Fibrin Sealant Application Systems." *Technology and Health Care* 10 (2002): 401-411.

D A. Fancy and T. Kodadek "Chemistry for the analysis of protein-protein interactions: Rapid and efficient cross-linking triggered by long wavelength light." *Proc. Natl. Acad. Sci.* Vol. 96, pp. 6020-6024, May 1999

Jackson, M. R. "Fibrin Sealants in Surgical Practice: An Overview." *American Journal of Surgery* 182 (August 2001) (2 Suppl): 1S-7S.

Khadem, J., Veloso, A. A., Tolentino, F. T., Hasan, T. and Hamblin, M. R., "Photodynamic Tissue Adhesion with Chlorin$_{e6}$, Protein Conjugates". *IOVS*, December 1999, Vol. 40, No. 13.

Lee, K-C, park, S-K and Lee, K-S (1991) neurosurgical applications of fibrin sealants. 9$^{th}$ Annual congress of the world society of cardio-thoracic surgeons; November 1999, Lisbon, Spain.

Mankad, P. S., and M. Codispoti. "The Role of Fibrin Sealants in Hemostasis." *American Journal of Surgery* 182 (August 2001) (2 Suppl): 21S-28S.

Maronea Piero, Monzillob Vincenza, Segua Catia, Antoniazzic Elena, "Antibiotic-Impregnated Fibrin Glue in Ocular Surgery: In vitro Antibacterial Activity", Ophthalmologica 1999; 213:12-15.

Matras, H (1985) Fibrin seal: the state of the art. J Oral Maxillofac Surg 43: 605-611.

Milne, A A, Murphy, W G, Reading, S J and Ruckley, C V (1995) Fibrin sealant reduces suture line bleeding during carotid endarterectomy: a randomised trial. Eur J Endovasc Surg 10: 91-94

Morikawa, T. "Tissue Sealing." *American Journal of Surgery* 182 (August 2001) (2 Suppl): 29S-35S.

Spotnitz, W D (1995) Fibrin sealant in the United States: clinical use at the University of Virginia. Thromb Haemost 74: 482-485.

Nishimotol Kazuo, Yamamura Keiko, Fukase Fumiaki, Kobayashil Masayoshi, Nishikimil Naomichi and Komoril Kimihiro, "Subcutaneous tissue release of amikacin from a fibrin glue/polyurethane graft", Journal of Infection and Chemotherapy; Vol. 10, No. 2 (2004) pages 101-104.

Yoshida H, Yamaoka, Y., Shinoyama M., Biol Pharm Bull. 2000; pages 371-374 "Novel drug delivery system using autologous fibrin glue-release properties of anti cancer drugs", Department of Pharmacy, Yamaguchi University Hospital, Ube, Japan.

The invention claimed is:

1. A method of treating damaged tissue, the method comprising:

applying a closure, the closure comprising a substrate suitable for application to a wound to stem bleeding, wherein said substrate is selected from the group consisting of a collagen sheet, bandage, gauze, cloth, tampon, membrane or sponge and is impregnated or coated with a tissue adhesive, said tissue adhesive comprising a matrix protein selected from the group consisting of fibrinogen, fibrin, collagen, fibronectin, keratin and laminin, or admixtures thereof, a photoactivatable metal-ligand complex and an electron acceptor; and irradiating the closure, thereby causing a cross-linking reaction between one of more matrix proteins within or coating the closure and the surrounding patient tissue.

2. The method of claim 1, wherein the photoactivatable metal-ligand is selected from the group consisting of Ru(II), Pd(II), Cu(II), NI(II), Mn(II) and Fe(III) complexes.

3. The method of claim 2, wherein the complex is selected from the group consisting of an Ru(II) bipyridyl complex, a Pd(II) porphyrin complex, a sulfonatophenyl Mn(II) complex and a Fe(III) protoporphyrin complex.

4. The method of claim 3, wherein the complex is a tris(bipyridyl) Ru(II) complex.

5. The method of claim 1, wherein the electron acceptor is selected from the group consisting of a persulfate, periodate, perbromate and a perchlorate compound.

6. The method of claim 1, wherein the closure further comprise a drug.

7. The method of claim 1, further comprising:

moving a first tissue portion in contact with a second tissue portion, such that upon irradiation the tissue adhesive forms a seal between the first tissue portion and the second tissue portion.

\* \* \* \* \*

UNITED STATES PATENT AND TRADEMARK OFFICE
CERTIFICATE OF CORRECTION

| | | |
|---|---|---|
| PATENT NO. | : 9,579,415 B2 | Page 1 of 1 |
| APPLICATION NO. | : 12/223945 | |
| DATED | : February 28, 2017 | |
| INVENTOR(S) | : Alan George Brownlee | |

It is certified that error appears in the above-identified patent and that said Letters Patent is hereby corrected as shown below:

On the Title Page

Assignee Item (73) change --Cook Incorporated-- to "Cook Medical Technologies LLC, 750 North Daniels Way, Bloomington, Indiana 47404".

Signed and Sealed this
Eleventh Day of April, 2017

Michelle K. Lee
*Director of the United States Patent and Trademark Office*